US010721986B2

(12) United States Patent
Prezioso

(10) Patent No.: US 10,721,986 B2
(45) Date of Patent: Jul. 28, 2020

(54) ADJUSTABLE HEADWEAR VISOR

(71) Applicant: Leonardo German Prezioso, Newhall, CT (US)

(72) Inventor: Leonardo German Prezioso, Newhall, CT (US)

(73) Assignee: Leonardo German Prezioso, Newhaven, CA (US)

( * ) Notice: Subject to any disclaimer, the term of this patent is extended or adjusted under 35 U.S.C. 154(b) by 0 days.

(21) Appl. No.: 15/667,010

(22) Filed: Aug. 2, 2017

(65) Prior Publication Data

US 2019/0037950 A1    Feb. 7, 2019

(51) Int. Cl.
*A42B 1/06* (2006.01)
*A42B 1/00* (2006.01)
*A61F 9/04* (2006.01)

(52) U.S. Cl.
CPC .............. *A42B 1/064* (2013.01); *A42B 1/004* (2013.01); *A42B 1/065* (2013.01); *A61F 9/045* (2013.01)

(58) Field of Classification Search
CPC ......... A42B 1/064; A42B 1/065; A42B 1/067; A42B 1/206; A42B 1/201; A61F 9/045
See application file for complete search history.

(56) References Cited

U.S. PATENT DOCUMENTS

| | | | | |
|---|---|---|---|---|
| 5,075,898 A | * | 12/1991 | Bedient | A42B 1/065 2/10 |
| 5,197,150 A | * | 3/1993 | Bedient | A42B 1/065 2/10 |
| 5,689,830 A | * | 11/1997 | Pflum | A42B 1/065 2/10 |
| 6,202,218 B1 | * | 3/2001 | Chen | A42B 1/065 2/175.1 |

FOREIGN PATENT DOCUMENTS

| | | | |
|---|---|---|---|
| CN | 206025322 U | * | 3/2017 |
| KR | 200473556 A | * | 7/2014 |
| KR | 101623886 A | * | 5/2016 |

OTHER PUBLICATIONS

Telescopic Mountain Biking Baseball Hat; https://www.lightinthebox.com/en/p/women-s-summer-sunscreen-camouflage-printed-beach-telescopic-mountain-biking-baseball-hat-sports-empty-cap_p5751498.html; accessed Mar. 6, 2019; published Apr. 28, 2017. (Year: 2017).*

* cited by examiner

*Primary Examiner* — Daniel J Colilla

(57) ABSTRACT

An apparatus for a baseball hat or golf visor comprised of a main body, which is made up of a top and a bottom creating a 'pocket'. An extensible visor is placed within the main body. A centrally located slot within the lower portion of the pocket, and a stabilizing tab within the visor allows the visor to be extended or retracted as desired.

1 Claim, 5 Drawing Sheets

ADJUSTABLE HEADWEAR VISOR

BACKGROUND OF THE INVENTION

The invention relates to an apparatus referred to as an Adjustable Headwear Visor that houses an extensible visor for added shading area.

SUMMARY OF THE INVENTION

The goal of the invention is to provide hat manufacturers with an apparatus referred to as an Adjustable Headwear Visor that can be sown into the visor area of the manufacturer's baseball hat or golf visor. The Adjustable Headwear Visor is intended to increase the user's shading area by allowing the user to extend the visor beyond the distance of a standard visor found in a baseball hat or golf visor.

DETAILED DESCRIPTION OF THE INVENTION

Figure 2:
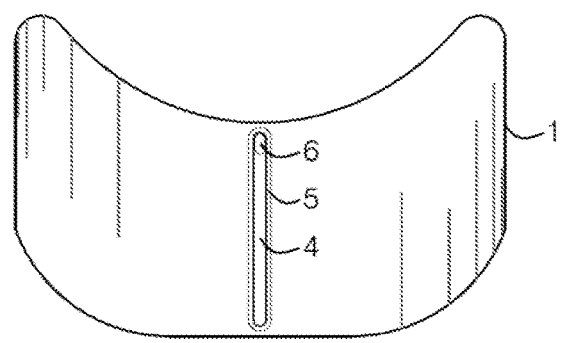
FIG. 2 is the lower portion of the main body for the Adjustable Headwear Visor that forms the pocket.
Figure 1:
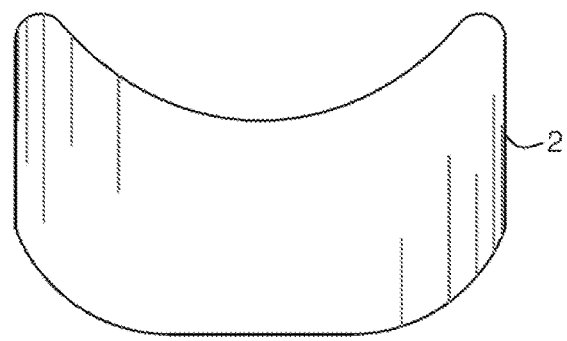
FIG. 1 is the upper portion of the main body for the Adjustable Headwear Visor that forms the pocket.
Figure 5:
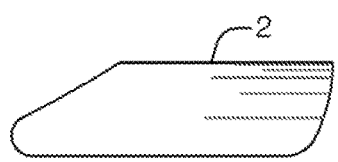
FIG. 5 is a left side view of the Adjustable Headwear Visor assembly.
Figure 3:
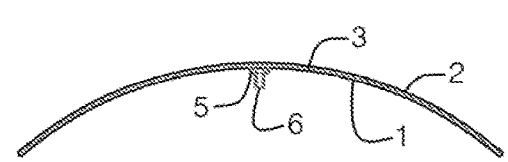
FIG. 3 is a front view of the Adjustable Headwear Visor assembly.
Figure 4:
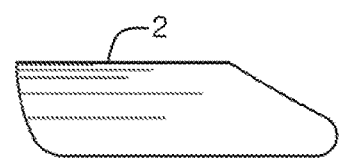
FIG. 4 is a right side view of the Adjustable Headwear Visor assembly.
Figure 7:
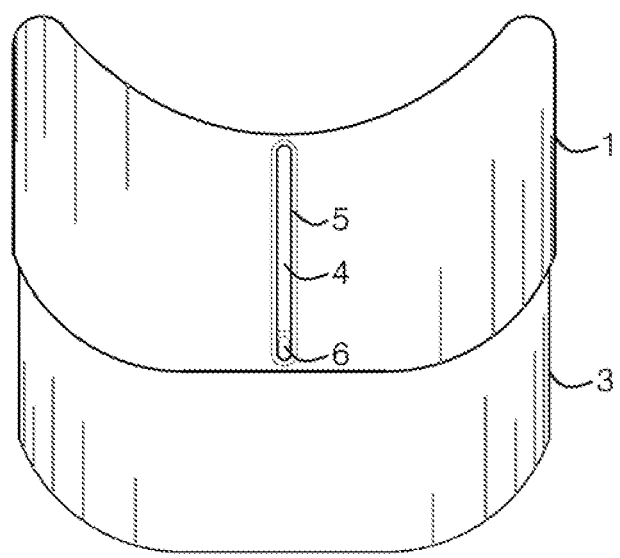
FIG. 7 is a bottom view of the main body assembly with the Adjustable Headwear Visor in its extended state.
Figures 6, 8, 9:
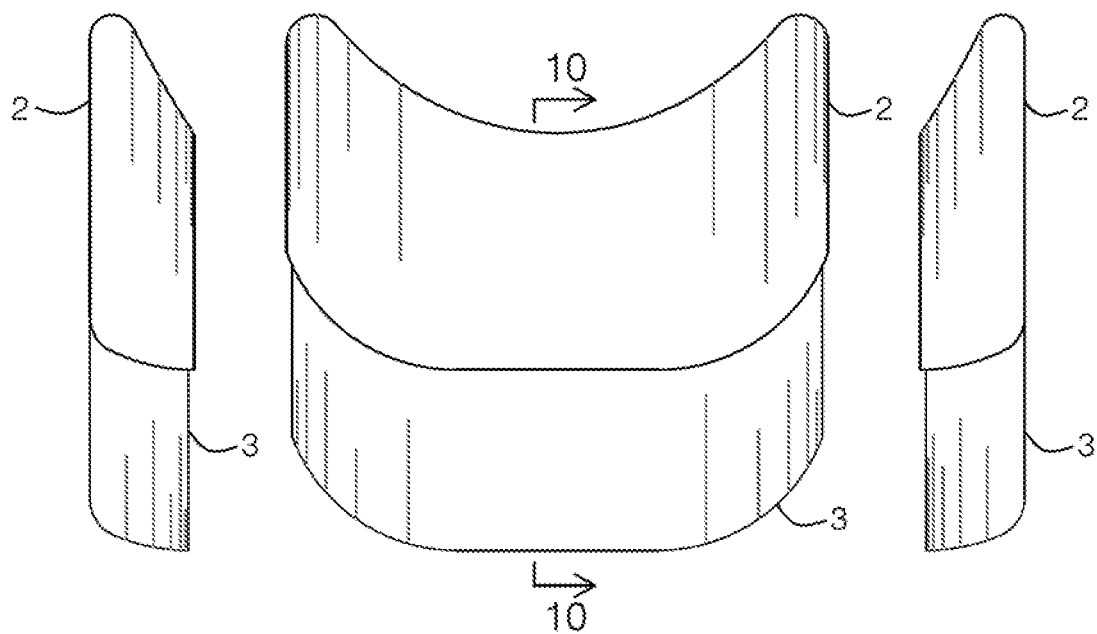
FIG. 6 is a top view of the main body assembly with the Adjustable Headwear Visor in its extended state.
FIG. 8 is a right side view of the main body assembly with the Adjustable Headwear Visor in its extended state.
FIG. 9 is a left side view of the main body assembly with the Adjustable Headwear Visor in its extended state.

Referring to FIG. 6 and FIG. 7, the Adjustable Headwear Visor is comprised of a main body that forms a pocket 1 and 2. An adjustable visor 3 fits within the pocket and is kept in place by a tab 6, which is molded as part of the adjustable visor 3.

When the three parts 1, 2 and 3 are sandwiched together, the main body 1 and 2 are snapped together unifying all three parts.

The tab 6 is used for extending and retracting the adjustable visor 3, via the slot 4. The thickened edges of the slot 5 help keep the tab 6 aligned, therefore keeping the adjustable visor 3 aligned for ease of extending or retracting it from the main body comprised of 1 and 2.

When worn, a person's fingertip is used to extend and retract the visor by using the tab 6, which is centrally and visibly located underneath the visor assembly.

Figure 10:
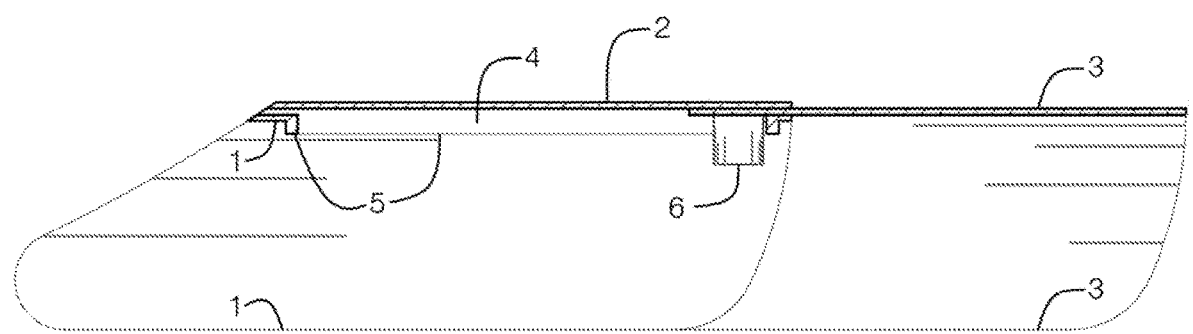
FIG. 10 is a sectional view illustrating the adjustable visor in its extended state.
Figure 11:
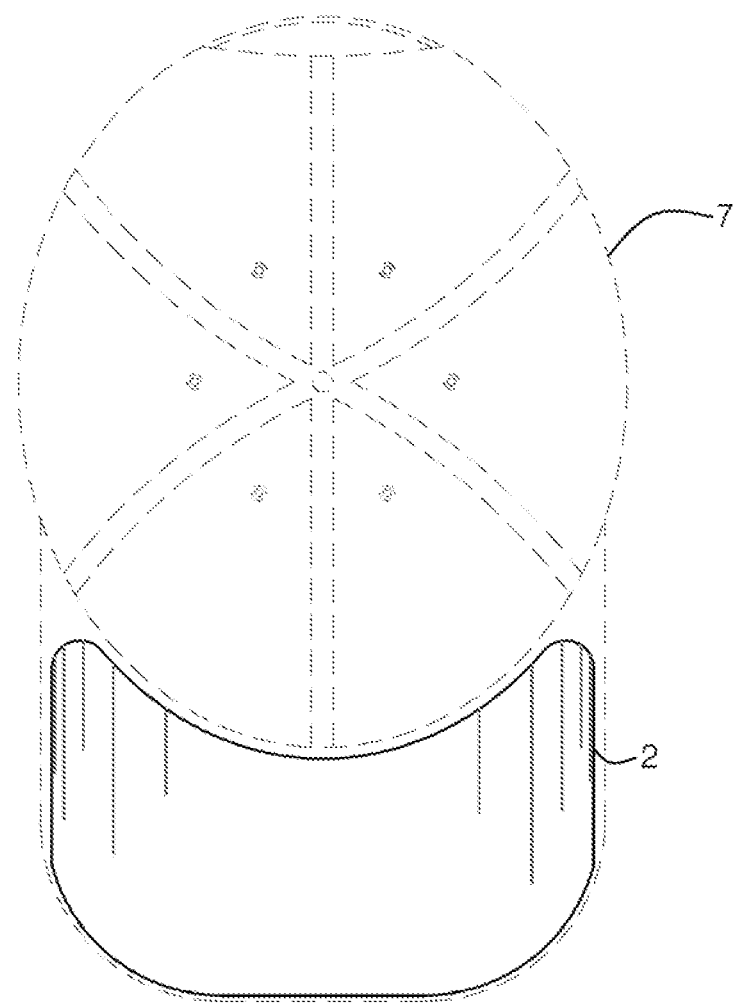
FIG. 11 is a top view of the Adjustable Headwear Visor assembly embedded within a baseball hat which is shown in broken lines since it forms no part of the apparatus sought to be patented.

Referring to FIG. 10, the adjustable visor 3 is fully extended when the tab 6 touches the front of the slot 4. This stops the adjustable visor from falling out of the main body. The adjustable visor is fully retracted when the tab 6 touches the back of the slot 4.

Figure 12:
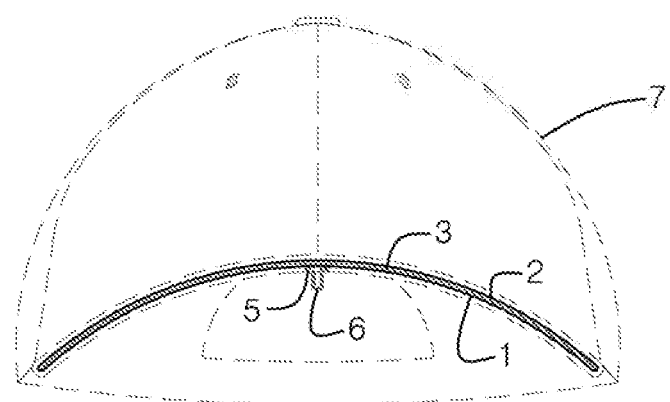
FIG. 12 is a front view of the Adjustable Headwear Visor assembly embedded within a baseball hat which is shown in broken lines since it forms no part of the apparatus sought to be patented.
Figure 13:
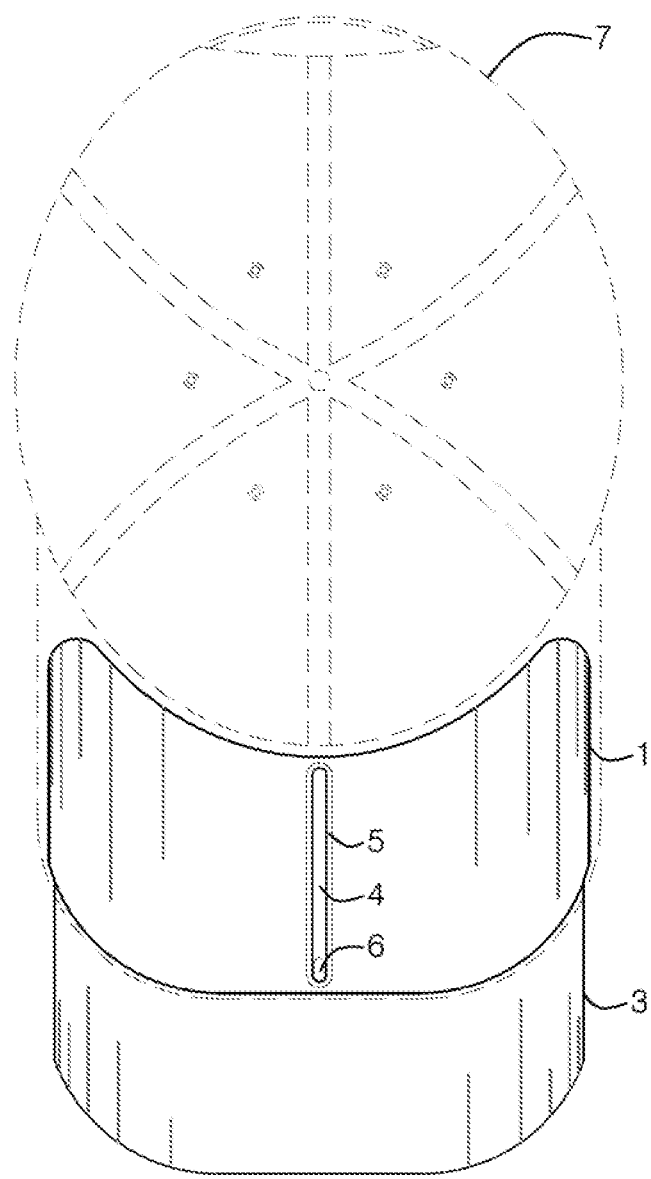
FIG. 13 is a bottom view of the Adjustable Headwear Visor assembly embedded within a baseball hat which is shown in broken lines since it forms no part of the apparatus sought to be patented.
Figure 14:
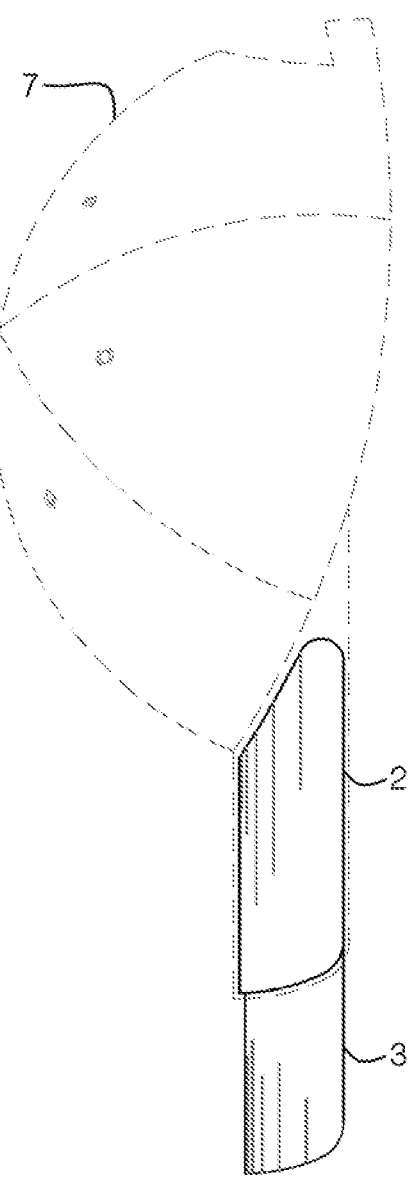
FIG. 14 is a right side view of the Adjustable Headwear Visor assembly embedded within a baseball hat which is shown in broken lines since it forms no part of the apparatus sought to be patented.

Referring to FIG. 12, the Adjustable Headwear Visor assembly is preformed with a curvature, so that it can be installed within a manufacturer's baseball hat or golf visor.

I claim:

1. An extensible visor apparatus for attaching to a baseball hat or visor, the extensible visor apparatus comprising:
    a main body including a top layer and a bottom layer forming a pocket therebetween, wherein the main body is configured to be attached to an underside of a baseball hat or visor;
    a centrally located slot within the lower portion of the main body;
    an extensible visor located within the pocket;
    a knob attached to the extensible visor and extending through the centrally located slot, wherein the extensible visor is configured to extend out of the pocket, away from the hat or visor, by manual sliding of the knob in the centrally located slot, whereby the shade provided by the baseball hat or visor to which the extensible visor apparatus is attached, is increased.

* * * * *